United States Patent
Kawahara et al.

(10) Patent No.: US 6,822,111 B2
(45) Date of Patent: Nov. 23, 2004

(54) PROCESS FOR PRODUCTION OF ASPARTYL DIPEPTIDE ESTER DERIVATIVES

(75) Inventors: Shigeru Kawahara, Kawasaki (JP); Kazutaka Nagashima, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/286,840

(22) Filed: Nov. 4, 2002

(65) Prior Publication Data

US 2003/0118710 A1 Jun. 26, 2003

Related U.S. Application Data

(63) Continuation of application No. PCT/JP01/03479, filed on Apr. 23, 2001.

(30) Foreign Application Priority Data

May 10, 2000 (JP) ........................................ 2000-137028

(51) Int. Cl.$^7$ ............................................. C07C 229/00
(52) U.S. Cl. ......................................................... 560/40
(58) Field of Search .......................................... 560/40

(56) References Cited

U.S. PATENT DOCUMENTS

| 5,480,668 | A | 1/1996 | Nofre et al. |
|---|---|---|---|
| 5,723,165 | A | 3/1998 | Takemoto et al. |
| 5,723,651 | A | 3/1998 | Hijiya et al. |
| 5,795,612 | A | 8/1998 | Takemoto et al. |
| 5,958,496 | A | 9/1999 | Amino et al. |
| 5,968,581 | A | 10/1999 | Nakamura et al. |
| 6,010,733 | A | 1/2000 | Takemoto et al. |
| 6,335,461 | B1 | 1/2002 | Amino et al. |
| 6,548,096 | B1 | 4/2003 | Amino et al. |
| 6,630,191 | B1 | 10/2003 | Amino et al. |
| 6,693,214 | B2 | 2/2004 | Kawahara et al. |
| 2002/0133037 | A1 | 9/2002 | Nagashima et al. |

FOREIGN PATENT DOCUMENTS

| EP | 1 070 726 A1 | 1/2001 |
|---|---|---|
| JP | 02/202855 | 8/1990 |
| JP | 05-178802 | 7/1993 |
| WO | WO 94/11391 | 5/1994 |
| WO | WO 99/52937 | 10/1999 |
| WO | WO 01/25260 | 4/2001 |

*Primary Examiner*—Paul A. Zucker
(74) *Attorney, Agent, or Firm*—Oblon, Spivak, McClelland, Maier & Neustadt, P.C.

(57) ABSTRACT

N-[N-[3-(phenyl having various substituent group(s) on the benzene ring)propyl]-L-α-aspartyl]-L-phenylalanine 1-methyl ester derivatives, which are useful as sweeteners, may be conveniently produced on an industrial scale at a high yield by reductively alkylating aspartame with a 3-(phenyl having specified substituent group(s) on the benzene ring)-2-propenyl aldehyde and hydrogen in the presence of a catalyst and a base.

26 Claims, No Drawings

PROCESS FOR PRODUCTION OF ASPARTYL DIPEPTIDE ESTER DERIVATIVES

CROSS REFERENCES TO RELATED APPLICATIONS

This application is continuation of International Patent Application No. PCT/JP01/03479, filed on Apr. 23, 2001, and claims priority to Japanese Patent Application No. 2000-137028, filed on May 10, 2000, both of which are incorporated herein by reference in their entireties.

BACKGROUND OF THE INVENTION

1. Field of the Invention

The present invention relates to novel processes for producing aspartyl dipeptide ester derivatives, which are useful as sweeteners.

2. Discussion of the Background

In recent years, as eating habits have been improved to a high level, obesity caused by excessive sugar intake and the diseases accompanied by obesity have become a serious health issue. Accordingly, the development of low-calorie sweeteners (sweetening agent) that replace sugar has been strongly in demand. As a sweetener that is widely used at present, there is aspartame which is excellent in safety and quality of sweetness, but however, is somewhat problematic in stability.

Against this background, certain N-[N-(phenylpropyl having various and specified substituent group(s) on the benzene ring)-L-α-aspartyl]-L-phenylalanine 1-methyl esters (aspartame derivatives) have been found to be sweeteners which are excellent in stability and, moreover, are better by far in degree of sweetness, i.e., have an advantage in cost per degree of sweet taste, (see, International Patent Publication WO99/52937). However, no method for the efficient process for production of these sweeteners is, as yet, known.

N-[N-(3-phenylpropyl)-L-α-aspartyl]-L-phenylalanine 1-methyl ester and N-[N-(3-methoxy-4-hydroxyphenylpropyl)-L-α-aspartyl]-L-phenylalanine 1-methyl ester, which are poor in a degree (potency) of sweetness as compared to these compounds, are described in the International Patent Publication WO94/11391. However, in this publication, no examples which would show a suitable operation for the synthesis thereof including the starting material employed is provided, and there is no mention of any process for the production of these compounds.

Meanwhile, a process which comprises reductively alkylating aspartame with a 3-(phenyl having various substituent group(s) on the benzene ring)-2-propenyl aldehyde and hydrogen in the presence of a catalyst has been proposed by some of the present inventors and the like for production of the above-mentioned aspartame derivatives which are useful as sweeteners (see, Japanese Patent Application No. 11-287398 and International No. PCT/JP00/06626 description). However, there remains a need for a process which affords these compounds with a further improvement in yield.

SUMMARY OF THE INVENTION

Accordingly, it is one object of the present invention to provide novel processes for the production of N-[N-(phenylpropyl having various and specified substituent group(s) on the benzene ring)-L-α-aspartyl]-L-phenylalanine 1-methyl esters (aspartame derivatives) which are useful as sweeteners and which yields these compounds in an improved yield.

In particular, it is another object of the present invention to provide novel processes which afford improved yields of the compounds of formula (2):

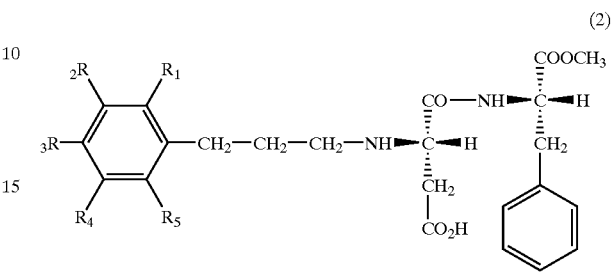

wherein in formula (2) $R_1$, $R_2$, $R_3$, $R_4$ and $R_5$ are each independently of each other a substituent selected from the group consisting of a hydrogen atom, a hydroxyl group, an alkoxy group having 1 to 3 carbon atoms, an alkyl group having 1 to 3 carbon atoms, and a hydroxyalkyloxy group having 2 or 3 carbon atoms, wherein two symbols of $R_1$ and $R_2$, or two symbols of $R_2$ and $R_3$ may be combined together to denote a methylenedioxy group.

It is another object of the present invention to provide an efficient and industrial process for producing such compounds.

These and other objects, which will become apparent during the following detailed description, have been achieved by the inventors' discovery that N-[N-(phenylpropyl having various and specified substituent group(s) on the benzene ring)-L-α-aspartyl]-L-phenylalanine 1-methyl esters (aspartame derivatives), more specifically aspartyl dipeptide ester derivatives represented by the general formula (2):

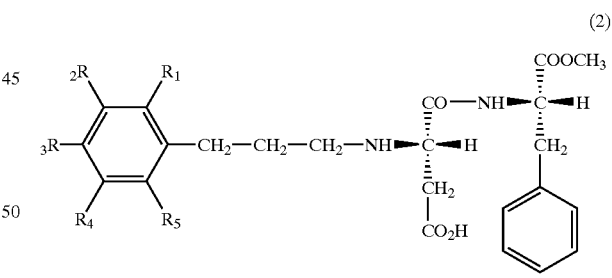

wherein in formula (2) $R_1$, $R_2$, $R_3$, $R_4$ and $R_5$ are each independently of each other a substituent selected from the group consisting of a hydrogen atom, a hydroxyl group, an alkoxy group having 1 to 3 carbon atoms, an alkyl group having 1 to 3 carbon atoms, and a hydroxyalkyloxy group having 2 or 3 carbon atoms, wherein two symbols of $R_1$ and $R_2$, or two symbols of $R_2$ and $R_3$ may be combined together to denote a methylenedioxy group, can be easily produced by reductively alkylating aspartame in the presence of a base and a catalyst, with an aldehyde represented by the following general formula (1) and hydrogen:

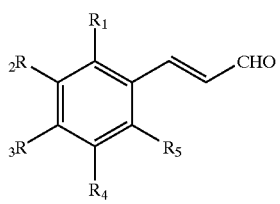

(1)

wherein in formula (1), $R_1$, $R_2$, $R_3$, $R_4$ and $R_5$ are each independently of each other a substituent selected from the group consisting of a hydrogen atom, a hydroxyl group, an alkoxy group having 1 to 3 carbon atoms, an alkyl group having 1 to 3 carbon atoms, a benzyloxy group and a hydroxyalkyloxy group having 2 or 3 carbon atoms, wherein two symbols of $R_1$ and $R_2$, or two symbols of $R_2$ and $R_3$ may be combined together to denote a methylenedioxy group, and the hydroxyl group (—OH) may denote a substituent group (—OM; M=metal atom) in its derivative form where the hydrogen atom in said hydroxyl group has been replaced by a metal atom, and where necessary neutralizing the product with an acid.

That is, the present invention provides the following embodiments and aspects:

(1) A process for producing an aspartyl dipeptide ester derivative represented by the following general formula (2):

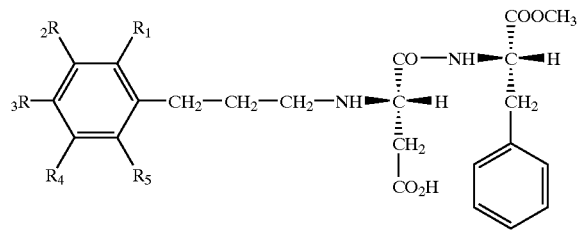

(2)

wherein in formula (2) $R_1$, $R_2$, $R_3$, $R_4$ and $R_5$ are each independently of each other a substituent selected from the group consisting of a hydrogen atom, a hydroxyl group, an alkoxy group having 1 to 3 carbon atoms, an alkyl group having 1 to 3 carbon atoms, and a hydroxyalkyloxy group having 2 or 3 carbon atoms, wherein two symbols of $R_1$ and $R_2$, or two symbols of $R_2$ and $R_3$ may be combined together to denote a methylenedioxy group, which comprises:

reductively alkylating aspartame with an aldehyde represented by the following general formula (1), and hydrogen in the presence of a catalyst and a base:

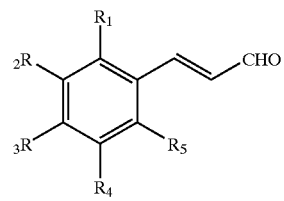

(1)

wherein in formula (1), $R_1$, $R_2$, $R_3$, $R_4$ and $R_5$ are each independently of each other a substituent selected from the group consisting of a hydrogen atom, a hydroxyl group, an alkoxy group having 1 to 3 carbon atoms, an alkyl group having 1 to 3 carbon atoms, a benzyloxy group and a hydroxyalkyloxy group having 2 or 3 carbon atoms, wherein two symbols of $R_1$ and $R_2$, or two symbols of $R_2$ and $R_3$ may be combined together to denote a methylenedioxy group, and the hydroxyl group (—OH) may denote a substituent group (—OM; M=metal atom) in its derivative form where the hydrogen atom in said hydroxyl group has been replaced by a metal atom.

Said derivative of formula (2) may be in any form of the free form and the salt form.

Accordingly, the object compound can be produced and obtained in the salt form through the reductive alkylation reaction. Where necessary or desired, the salt form may be further converted into the free form, whereby the object compound can be produced and obtained. Any such form of the object compound and any such process therefor are contained in the present invention. To the present invention, in addition to the reductive alkylation reaction process, any usual and conventional process, such as a salt-formation process, a desalination process, and/or a purification process may be added so long as the object thereof is not inhibited or impaired.

Incidentally, in the case when the aldehyde of formula (1) used as the starting material contains a benzyloxy group, the benzyloxy group is converted into a hydroxyl group by the removal of the benzyl group in the benzyloxy moiety, and thereby the object compound of formula (2) obtained after the reaction does not contain a benzyloxy group, and instead contains a hydroxyl group.

(2) The process (1) as defined above, wherein said derivative of formula (2) obtained as the object compound is in the free form.

In this case, the process includes a process for converting said derivative existing in the salt form obtained in the reductive alkylation reaction into that in the free form.

(3) The process (1) or (2) as defined above, wherein in said general formula (1), $R_1$, $R_2$, $R_3$, $R_4$ and $R_5$ are each independently of each other a substituent selected from the group consisting of a hydrogen atom, a hydroxyl group, a methoxy group, a methyl group and a benzyloxy group, and in said general formula (2), $R_1$, $R_2$, $R_3$, $R_4$ and $R_5$ are each independently of each other a substituent selected from the group consisting of a hydrogen atom, a hydroxyl group, a methoxy group and a methyl group.

(4) The process as defined in the process (1) to (3), wherein in the above process, the aldehyde of formula (1)

used as the starting material has a hydroxyl group on the benzene ring or the like, and at least one part (a portion) of hydrogen atoms in the hydroxyl groups of the aldehyde molecules has been replaced by a metal atom, and at least one part (a portion) of the aldehyde molecules wherein the hydroxyl group has been converted into metal alkoxide, is present as said base.

In the present invention, in the case when the aldehyde contains a hydroxyl group, and the hydroxyl group is converted to metal alkoxide, the aldehyde can also serve as all or a portion of the base. Therefore, in this case, the use of an additional base is not necessary. Moreover, the use of a surplus or excess of base is not preferred since a secondary reaction arises.

(5) The process as defined above, wherein in said formulae (1) and (2), $R_1$ is a hydrogen atom, a methyl group or a hydroxyl group, $R_2$ is a hydrogen atom, a methyl group or a hydroxyl group, $R_3$ is a methoxy group, and $R_4$ and $R_5$ are a hydrogen atom. In this process, in the aldehyde of formula (1), at least one of $R_1$ and $R_2$ may be a benzyloxy group. In particular, the process as defined above, particularly the process (1) to (4), wherein in the above formulae, $R_2$ is a hydrogen atom or a hydroxyl group, $R_3$ is a methoxy group, and $R_1$, $R_4$ and $R_5$ are a hydrogen atom, is preferred. Among them, the process as defined above, particularly the process (1) to (4), wherein in the above formulae, $R_1$, $R_4$ and $R_5$ are a hydrogen atom, $R_2$ is a hydroxyl group, $R_3$ is a methoxy group, is more preferred.

(6) The process as defined above, wherein in said formulae (1) and (2), $R_1$ is a hydrogen atom, a methyl group or a methoxy group, $R_2$ is a hydrogen atom, a methyl group or a methoxy group, $R_3$ is a hydroxyl group, and $R_4$ and $R_5$ are a hydrogen atom, and in the formula (1), $R_3$ may be a benzyloxy group. In particular, the process as defined above, particularly the process (1) to (4), wherein in the above formulae, $R_2$ is a hydrogen atom or a methoxy group, $R_3$ is a hydroxyl group, and $R_1$, $R_4$ and $R_5$ are a hydrogen atom, is preferred.

(7) The process as defined above, particularly the process (1) to (3), wherein said base is at least one selected from the group consisting of metal hydrides, metal alcoxides (alkoxides), metal hydroxides, and amines.

(8) The process (7) as defined above, wherein said metal hydride is selected from the group consisting of LiH, NaH, KH and the like, said metal alkoxide is selected from the group consisting of LiOMe, NaOMe, KOMe and the like, said metal hydroxide is selected from the group consisting of LiOH, NaOH, KOH, Mg(OH)$_2$ and the like, and said base is at least one of these compounds.

(9) The process (7) as defined above, wherein said amine is at least one of Et$_3$N and Et$_2$NH.

(10) The process as defined above, particularly the process (1) to (3), wherein said base is sodium hydroxide or potassium hydroxide.

(11) The process as defined above, particularly the process (1) to (3), which comprises a process for mixing said base with said aldehyde previously, i.e., prior to the addition of the aspartame.

(12) The process as defined above, particularly the process (1) to (4), wherein said aldehyde is a compound represented by the following general formula (3) or (4); or which comprises a process for conversion of a corresponding aldehyde into a compound represented by the following general formula (3) or (4):

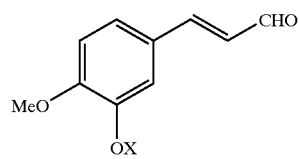

(3)

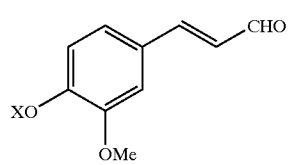

(4)

In the above formulae (3) and (4), X denotes any one of lithium atom, sodium atom and potassium atom. Me denotes a methyl group.

In this process, since the aldehyde can also concurrently serve as the base, in the reductive alkylation reaction with the aspartame, the use of an additional base (new base) is not necessary.

(13) The process as defined above, particularly the process (1) to (4), wherein said base is any one of a lithium compound, a sodium compound and/or a potassium compound, and the above described aldehyde is a compound represented by the following general formula (3') or (4'), and which comprises a process for mixing said aldehyde with said base previously (i.e., prior to the addition of the aspartame) to form a salt represented by the following general formula (3) or (4);

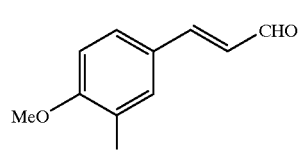

(3')

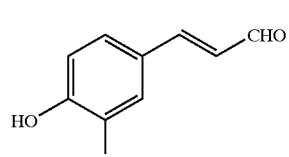

(4')

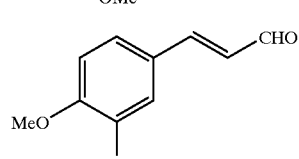

(3)

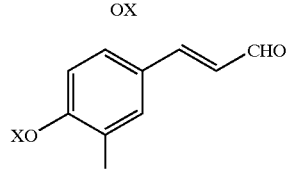

(4)

In the above formulae (3) and (4), X denotes any one of lithium atom, sodium atom and/or potassium atom. Me denotes a methyl group.

In this process, as in the one described immediately above, since the aldehyde can also concurrently serve as the base, in the reductive alkylation reaction with the aspartame, the use of an additional base is not necessary.

(14) The process as defined above, particularly the process (1) to (4), which comprises a process for converting the derivative of formula (2) existing in the salt form obtained in said reductive alkylation reaction, into said derivative existing in the free form through neutralization with an acid.

(15) The process (14) as defined above, wherein said acid is any one of hydrochloric acid, sulfuric acid, and/or acetic acid.

(16) The process (14) as defined above, wherein in said reductive alkylation reaction, the neutralization with an acid is conducted during a hydrogenation reaction.

(17) The process as defined above, particularly the process (1) to (4), wherein in said reductive alkylation reaction, the temperature for the hydrogenation reaction is in a range of 0 to 60° C.

(18) The process as defined above, particularly the process (1) to (4), which comprises in said reductive alkylation reaction, a process for retaining the reaction mixture while stirring for at least 10 minutes at a temperature of 40° C. or lower before the hydrogenation reaction.

(19) The process as defined above, particularly the process (1) to (4), which comprises in said reductive alkylation reaction, a process for removing at least one portion of any water contained in the solvent before the hydrogenation reaction.

(20) The process as defined above, particularly the process (1) to (4), wherein said catalyst is a catalyst for hydrogenation, and is at least one of palladium on carbon, palladium black, Raney Nickel, and/or platinum on carbon.

(21) The process as defined above, particularly the process (1) to (4), wherein said reaction is conducted in a solvent.

(22) The process (21) as defined above, wherein said solvent is alcohol, particularly methanol, or a mixed solvent of methanol with other solvent(s) (water-containing methanol and the like).

(23) The process as defined above, particularly the process (1) to (4), which comprises in said reductive alkylation reaction, a hydrogenation reaction with a hydrogen pressure of 0.1 to 10 MPa, preferably 0.1 to 1.0 MPa.

(24) The process as defined above, particularly the process (1) to (4), wherein the above described derivative of formula (2) as the object compound exists in the free form, and which comprises a process for crystallization of said derivative with a mixed solvent of water-alcohol after the process for production of the free form.

Through the crystallization process, the salt can be removed efficiently for purification.

(25) The process (24) as defined above, wherein the alcohol used for the above described solvent for crystallization (the mixed solvent) is a methanol.

DETAILED DESCRIPTION OF THE PREFERRED EMBODIMENTS

In the following, the preferred embodiments for carrying out the present invention, are described in more detail. However, it is to be understood that the typical processes thereof are mainly explained, and that the present invention is not limited thereto.

In the present invention, the reaction proceeds, by retaining the solution wherein aspartame and a specified aldehyde have been dissolved or dispersed in the presence of a base, at a suitable temperature and for a certain constant period (hours), adding a catalyst (a catalyst for hydrogenation) thereto, and stirring the solution under hydrogen gas atmosphere (hydrogenating). After this manner, the derivative of formula (2) can be obtained in the salt form. In order to obtain a free form thereof, during the hydrogenation reaction or after completion of the hydrogenation reaction, an acid is added thereto to neutralization, the catalyst is removed therefrom by filtration, and the filtrate is concentrated to obtain a crude product of the aspartyl dipeptide ester derivative of formula (2). Thereafter, through usual and common purification processes, such as re-crystallization and the like, the aspartyl dipeptide ester derivative (free form) as an objective can be easily obtained in pure form.

Incidentally, since the decomposition of aspartame proceeds under basic conditions, the method in which the aspartame is added to a solution in which the aldehyde and the base have been previously mixed, is preferable in view of preventing the aspartame from decomposing. In this case, when the aldehyde contains a hydroxyl group, particularly a phenolic hydroxyl group, by converting the phenolic hydroxyl group into a salt formation, such as that in a phenoxide or the like in advance and using the thus-converted product in the reaction, the alkylation with the aspartame can be conducted without adding any additional base thereto.

This method is preferable, also in view of the fact that a secondary reaction, for example, the formation of diketo piperadine (diketopiperazine) from the aspartame can be suppressed. This method is within the scope of the present invention as a matter of course.

As for the base used in the present invention, there is no particular limitation thereto. Therefore, any basic compound (inorganic base, organic base and the like) can be used therefor. For the base, a compound can be selected from, for example, metal hydrides, metal alcoxides (alkoxides), metal hydroxides, and an amines. For the metal hydride LiH, NaH, KH and the like can be used, for the metal alkoxide LiOMe, NaOMe, KOMe and the like can be used, and for the metal hydroxide LiOH, NaOH, KOH, Mg(OH)$_2$ and the like can be used. Among them, in view of the fact that its effectuation (use) can be conducted at a low price on an industrial scale, an inorganic base, such as sodium carbonate, sodium hydrogen carbonate, sodium hydroxide, lithium hydroxide, potassium hydroxide, magnesium hydroxide, sodium hydride, sodium methoxide and the like, and an organic amine, such as triethyl amine, diethyl amine and the like, are used preferably. Particularly, sodium hydroxide and potassium hydroxide are used more preferably.

In the reductive alkylation reaction of the present invention, the pH value of the solution before the hydrogenation reaction for reacting hydrogen is preferably 6.5 or higher, since a decomposition reaction proceeds when the value is much lower. More preferably, the pH value is in a range of 7.5 to 12 or so.

In the present invention, in the reductive alkylation reaction, the reaction mixture is retained before the hydrogenation reaction, while stirring, preferably at a temperature of 50° C. or lower for at least 10 minutes (10 minutes or longer), and more preferably at a temperature of −10 to 40° C. or so for 2 to 3 hours or so, desirably in view of prevention of secondary reactions.

As for the retention while stirring before the hydrogenation reaction, it is more effectively conducted by concentrating the solvent thereof to remove the water from the system of reaction. It is thought that through this method Schiff base formation with the aldehyde and the aspartame is promoted. As for the water content in the solvent thereof, preferably 10 weight % or less, and more preferably 5 to 0.1 weight % or so may be selected.

Further, for the solvent used in the present invention, it is preferable to select and use a solvent having low content of water therein. For the method for removal of water, a dehydrating agent can be also added thereto. For example, zeolite, "molecular sieve(s)" and the like may be also added thereto to be able to remove water therefrom.

As for the temperature and time for the reaction, any condition suitable for a hydrogenation reaction such as a reductive alkylation reaction can be selected therefor. For example, preferably a temperature range of 0 to 40° C. or so and a reaction time range of 2 to 72 hours or so, and more preferably a temperature range of 10 to 30° C. or so and a reaction time range of 10 to 48 hours or so can be selected in view of suppressing secondary reactions and promoting the reaction desired.

In the case when the object compound of formula (2) in the free form is obtained, a neutralization process is used. To the acid used in the neutralization, there is no particular limitation. Any inorganic acid and an organic acid which are conventionally used, can be used therefor. Acetic acid, hydrochloric acid, sulfuric acid, and the like are selected preferably therefor, because they can be used industrially at a low price.

In case that the derivative of formula (2) in the free form is obtained, the time for neutralization with an acid in the present invention is not limited to the time after completion of the hydrogenation reaction, and the neutralization can be conducted during the hydrogenation reaction. In this manner, rendering the reaction system acidic or neutral, the yield can be further improved. In this case, the reaction mixture is preferably adjusted to an acidic or neutral pH, preferably, at some time after the start of the hydrogenation reaction and after the reaction has proceeded for a definite period of time (after some elapsed time). For example, the neutralization may be conducted within a time period of 24 hours at 50° C. or lower from the start of the reaction Preferably, the neutralization can be conducted after an elapsed time of 1 to 6 hours or so at 0 to 35° C. or so from the start. It is preferable to conduct the neutralization after an elapsed time of 2 to 5 hours from the start of the hydrogenation, in view of preventing the decomposition of the starting materials, the product and the like.

In the case when an acid is added to the reaction mixture during the hydrogenation reaction, with respect to the subsequent hydrogenation reaction, the reaction may be further continued at a temperature of 10 to 50° C. or so for 15 to 48 hours or so.

As for the pH value of the reaction solution after the neutralization, in order to suppress the decomposition of the product, preferably a pH value of 2 to 8 or so, and more preferably a pH value of 3 to 7 or so may be employed.

As for the solvent employed in the reductive alkylation reaction in the present invention, there is no particular limitation thereto, and any solvent inactive to a basic substance for the reaction, the catalyst and the product may be employed therefor.

A homogeneous organic solvent which can dissolve aspartame and the aldehyde of formula (1) used for the starting material, and which is a single solvent consisting of one kind of organic solvent only or a mixed solvent consisted of plural kinds of organic solvents, or a mixture of such organic solvent with water may be employed therefor.

For the organic solvent, for example, alcohols such as methanol, ethanol and the like, tetrahydrofuran, toluene, methyl acetate and dimethylformamide may be used. A particularly preferable solvent is methanol.

As for the catalyst, a palladium-based catalyst, a platinum-based catalyst, a nickel-based catalyst and the like may be used. Specifically, palladium on carbon, palladium black, Raney Nickel, platinum on carbon and the like may be used. Particularly, a palladium-based catalyst, such as palladium on carbon, palladium black and the like is preferable.

The present reductive alkylation reaction can be conducted through hydrogenation (hydrogen addition), and in such case, for the hydrogen pressure, preferably 0.1 to 10 MPa or so, and more preferably 0.1 to 1 MPa or so may be selected.

In the case when the present reductive alkylation reaction is conducted under normal pressure, means for bubbling the reaction solution with hydrogen is preferable in view of promoting the reaction.

As for the molar ratio of the aspartame to the aldehyde used as the starting materials for the reaction, a range of preferably 0.5 to 3 moles or so, and more preferably 1 to 2 moles or so, of aspartame per 1 mole of the aldehyde can be used for reaction.

In the present invention, the derivative as the object compound can be obtained in the salt form or in the free form, after completion of the reductive alkylation reaction. As for the salt-formation process, the desalination process, and the process or means necessary for separation or purification thereof, they can be conducted easily in the usual manner. As described before, the derivatives thus obtained are all contained in the products which have been produced in the process of the present invention, as a matter of course.

Particularly, in the case when the object compound of formula (2) is purified for separation in the free form, the salt can be removed efficiently by crystallizing the object compound with the use of water-alcohol (methanol or the like) as a crystallization solvent.

According to the findings of the present inventors, the yield was low in the alkylation reaction of aspartame with a 3-(phenyl having various substituent group(s) on the benzene ring)-2-propenyl aldehyde. As the reasons thereto, it is thought that the Schiff base formed in the hydrogenation (hydrogen addition) is unstable and is decomposed, or that a secondary reaction (formation of alcohol) of said aldehyde arises. In the present invention, it is thought that by placing the base in the reaction system, a Schiff base is formed stably to suppress such a secondary reaction, and thereby the hydrogenation is promoted.

Other features of the invention will become apparent in the course of the following descriptions of exemplary embodiments which are given for illustration of the invention and are not intended to be limiting thereof.

EXAMPLES

Example 1

Production of N-[N-[3-(3-hydroxy-4-methoxyphenyl) propyl]-L-α-aspartyl]-L-phenylalanine 1-methyl Ester.

Aspartame (3.12 g, 10.2 mmol) and pelletized sodium hydroxide (0.45 g, 10.8 mmol) were added to methanol (100 ml), and the mixture was stirred at 30° C. for 10 minutes. To this solution, 3-(3-hydroxy-4-methoxyphenyl)-2-propenyl aldehyde (1.51 g, 8.59 mmol) was added, and then 10% palladium on carbon (dried product) (0.9 g) was added thereto, and the thus-obtained mixture was stirred under a hydrogen atmosphere of normal pressure (0.1 MPa) at 35° C. for 47 hours. The reaction solution was filtered to remove the catalyst, and the filtrate was neutralized with acetic acid and subjected to HPLC (High Performance Liquid Chromatography) to determine that the title compound was produced (2.04 g, 4.45 mmol, 51.8%).

Example 2

Production of N-[N-[3-(3-hydroxy-4-methoxyphenyl) propyl]-L-α-aspartyl]-L-phenylalanine 1-methyl Ester.

Pelletized sodium hydroxide (0.87 g, 20.9 mmol) and 3-(3-hydroxy-4-methoxyphenyl)-2-propenyl aldehyde (3.0 g, 17.0 mmol) were added to methanol (200 ml), and the mixture was stirred for a while to form a completely homogeneous solution. Aspartame (5.82 g, 19.8 mmol) was added thereto at room temperature to produce a slurry, and methanol (80 g) was removed therefrom by distillation under reduced pressure. Subsequently, 10% palladium on carbon (dried product) (0.77 g) was added thereto, and the thus-obtained mixture was stirred under a hydrogen atmosphere of normal pressure (0.1 MPa) at room temperature for 3 hours. After that, acetic acid (1.72 ml, 29.0 mmol) was added thereto, and the thus-obtained mixture was further stirred under a hydrogen atmosphere of normal pressure (0.1 MPa) at 45° C. for 21 hours. The reaction solution was filtered to remove the catalyst, and the filtrate was subjected to HPLC (High Performance Liquid Chromatography) to determine that the title compound was produced (4.18 g, 9.12 mmol, 53.6%).

Example 3

Production of N-[N-[3-(3-hydroxy-4-methoxyphenyl) propyl]-L-α-aspartyl]-L-phenylalanine 1-methyl Ester Pelletized sodium hydroxide (0.87 g, 20.9 mmol) and 3-(3-hydroxy-4-methoxyphenyl)-2-propenyl aldehyde (3.0 g, 17.0 mmol) were added to methanol (100 ml), and the mixture was stirred for a while to form a completely homogeneous solution. Aspartame (5.82 g, 19.8 mmol) was added thereto at room temperature, and then the thus-obtained mixture was stirred for 3 hours at 35° C. Subsequently, 10% palladium on carbon (dried product) (0.87 g) was added thereto, and the thus-obtained mixture was stirred under a hydrogen atmosphere of normal pressure (0.1 MPa) at 10° C. for 22 hours. After that, acetic acid (1.72 ml, 29.0 mmol) was added thereto, and the thus-obtained mixture was further stirred under a hydrogen atmosphere of normal pressure (0.1 MPa) at 35° C. for 21 hours. The reaction solution was filtered to remove the catalyst, and the filtrate was subjected to HPLC (High Performance Liquid Chromatography) to determine that the title compound was produced (4.95 g, 10.8 mmol, 63.5%).

Example 4

Production of N-[N-[3-(3-hydroxy-4-methoxyphenyl) propyl]-L-α-aspartyl]-L-phenylalanine 1-methyl Ester Pelletized sodium hydroxide (2.7 g, 64.8 mmol) and 3-(3-hydroxy-4-methoxyphenyl)-2-propenyl aldehyde (9.11 g, 51.0 mmol) were added to methanol (314 ml), and the mixture was stirred for a while to form a completely homogeneous solution. Aspartame (18.1 g, 61.4 mmol) was added thereto at room temperature. After that, the thus-obtained mixture was stirred for 3 hours at 10° C. Subsequently, 10% palladium on carbon (dried product) (2.7 g) was added thereto, and the thus-obtained reaction solution was stirred under bubbling with a hydrogen stream of 50 ml/minute at 10° C. for 6 hours. After that, acetic acid (5.35 g, 89.0 mmol) was added thereto, and the thus-obtained mixture was further stirred under a hydrogen atmosphere of normal pressure (0.1 MPa) at 35° C. for 17 hours. The reaction solution was filtered to remove the catalyst, and the filtrate was subjected to HPLC (High Performance Liquid Chromatography) to determination that the title compound was produced (16.4 g, 35.8 mmol, 70.1%).

Example 5

Production of N-[N-[3-(3-hydroxy-4-methoxyphenyl) propyl]-L-α-aspartyl]-L-phenylalanine 1-methyl Ester From the reduction reaction solution obtained in the Example 4, the solvent was removed by distillation under reduced pressure, and a mixed solvent (250 ml) of methanol and water (33% by volume) was added thereto. The mixture was stirred for a while at 60° C. to dissolve the residue completely. Subsequently, the thus-obtained solution was cooled down to 10° C. little by little to precipitate crystals. After that, the reaction mixture was held at the same temperature for 13 hours. The crystals thus obtained were filtered and dried to obtain N-[N-[3-(3-hydroxy-4-methoxyphenyl) propyl]-L-α-aspartyl]-L-phenylalanine 1-methyl ester in the crystalline form (12.7 g).

Example 6

Production of N-[N-[3-(4-hydroxy-3-methoxyphenyl) propyl]-L-α-aspartyl]-L-phenylalanine 1-methyl Ester Pelletized sodium hydroxide (0.86 g, 20.64 mmol) and 3-(4-hydroxy-3-methoxyphenyl)-2-propenyl aldehyde (3.00 g, 16.7 mmol) were added to methanol (105 ml), and the mixture was stirred for a while to produce a completely homogeneous solution. Aspartame (6.1 g, 20.7 mmol) was added thereto at 10° C. After that, the thus-obtained mixture was stirred for 2.5 hours at the same temperature. Subsequently, 10% palladium on carbon with a water content of 50% (1.89 g) was added thereto, and the thus-obtained reaction solution was stirred under a hydrogen atmosphere of 0.7 MPa at 10° C. for 5 hours. After that, acetic acid (1.62 ml, 27.2 mmol) was added thereto, and the thus-obtained mixture was further stirred under a hydrogen atmosphere of 0.7 MPa at 35° C. for 12 hours. The reaction solution was filtered to remove the catalyst, and the filtrate was subjected to HPLC to determination that the title compound was produced (5.05 g, 11.0 mmol, 66.0%).

Comparative Example 1

Production of N-[N-[3-(3-hydroxy-4-methoxyphenyl) propyl]-L-α-aspartyl]-L-phenylalanine 1-methyl Ester Aspartame (0.40 g, 1.47 mmol) and 3-(3-hydroxy-4-methoxyphenyl)-2-propenyl aldehyde (0.25 g, 1.40 mmol) were added to methanol (13 ml), and the mixture was stirred for a while. To the thus-obtained slurry, 10% palladium on carbon in the water content of 50% (0.12 g) was added thereto, and the thus-obtained mixture was stirred under a hydrogen atmosphere of normal pressure (0.1 MPa) at room temperature for 24 hours. The reaction solution was filtered to remove the catalyst, and the filtrate was subjected to HPLC (High Performance Liquid Chromatography) to determine that the title compound was produced (0.21 g, 0.46 mmol, 32.8%).

According to the present invention, aspartyl dipeptide ester derivatives useful as a sweetener, that is, an N-[N-[3-(phenyl having various substituent group(s) on the benzene ring) propyl]-L-α-aspartyl]-L-phenylalanine 1-methyl ester derivatives represented by the above described general formula (2) can be produced industrially and conveniently also at a good yield.

What is claimed is:

1. A process for producing an aspartyl dipeptide ester derivative represented by formula (2):

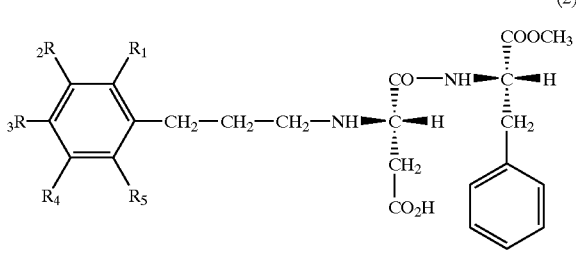

(2)

wherein said compound is in any form of the free form and the salt form, said process comprising:

reductively alkylating aspartame with an aldehyde represented by formula (1), and hydrogen in the presence of a catalyst and a base:

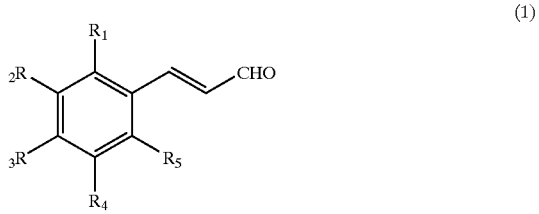

(1)

wherein said base is at least one member selected from the group consisting of metal hydrides, metal alkoxides, metal hydrozides, diethylamine, triethylamine, sodium carbonate, sodium hydrogen carbonate, and mixtures thereof, and wherein $R_1$, $R_2$, $R_3$, $R_4$, and $R_5$ satisfy one of the following definitions (a), (b), (c), or (d):

(a) in said formulae (1) and (2), $R_1$ is a hydrogen atom, a methyl group or a methoxy group, $R_2$ is a hydrogen atom, a methyl group or a methoxy group, $R_3$ is a hydroxyl group, and $R_4$ and $R_5$ are a hydrogen atom;

(b) in said formulae (1) and (2), $R_1$, $R_4$ and $R_5$ are a hydrogen atom, $R_2$ is a hydroxyl group, and $R_3$ is a methoxy group;

(c) in said formula (2), $R_1$ is a hydrogen atom, a methyl group or a methoxy group, $R_2$ is a hydrogen atom, a methyl group or a methoxy group, $R_3$ is a hydroxyl group, and $R_4$ and $R_5$ are a hydrogen atom, and in said formula (1), $R_1$ is a hydrogen atom, a methyl group or a methoxy group, $R_2$ is a hydrogen atom, a methyl group or a methoxy group, $R_3$ is a benzyloxy group, and $R_4$ and $R_5$ are a hydrogen atom; or (d) in said formula (2), $R_1$, $R_4$ and $R_5$ are a hydrogen atom, $R_2$ is a hydroxyl group, and $R_3$ is a methoxy group, and in said formula (1), $R_1$, $R_4$ and $R_5$ are a hydrogen atom, $R_2$ is a benzyloxy group, and $R_3$ is a methoxy group.

2. The process of claim 1, wherein in formulae (1) and (2), $R_1$ is a hydrogen atom, a methyl group or a methoxy group, $R_2$ is a hydrogen atom, a methyl group or a methoxy group, $R_3$ is a hydroxyl group, and $R_4$ and $R_5$ are a hydrogen atom.

3. The process of claim 1, wherein in said formulae (1) and (2), $R_1$, $R_4$ and $R_5$ are a hydrogen atom, $R_2$ is a hydroxyl group, and $R_3$ is a methoxy group.

4. The process of claim 1, wherein said aspartyl dipeptide ester compound is in the free form, and which comprises a process for converting said compound from the salt form into the free form.

5. The process of claim 1, wherein said aldehyde has a hydroxyl group, and wherein at least a portion of hydrogen atoms in said hydroxyl groups of the aldehyde molecules is replaced by a metal atom, and at least a portion of said aldehyde molecules in which the hydroxyl group has been converted into metal alkoxide, is present as said base.

6. The process of claim 1, wherein the base is sodium hydroxide or potassium hydroxide.

7. The process of claim 1, which further comprises mixing said base with said aldehyde prior to addition of said aspartame.

8. The process of claim 1, which further comprises a process for converting said aldehyde into a compound represented by the following general formula (3) or (4);

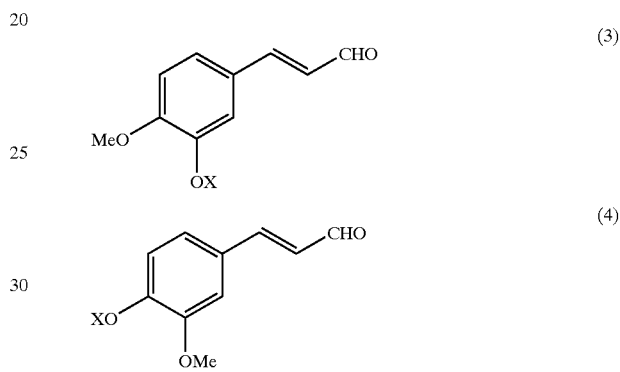

wherein in the above formulae (3) and (4), X denotes any one of lithium atom, sodium atom, and potassium atom.

9. The process of claim 1, wherein said base is selected from the group consisting of lithium compounds, sodium compounds, and potassium compounds, and wherein said aldehyde is an aldehyde represented by the formula (3') or (4'), and which further comprises a process for mixing said aldehyde with said base prior to addition of said aspartame to form a salt represented by the following general formula (3) or (4);

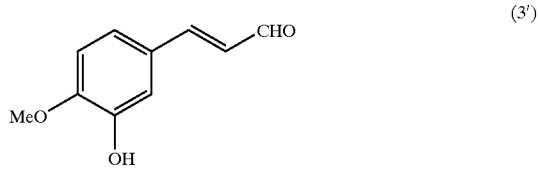

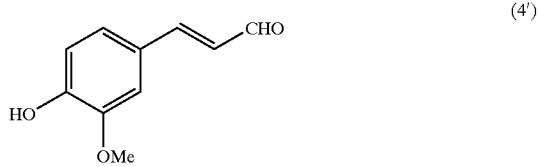

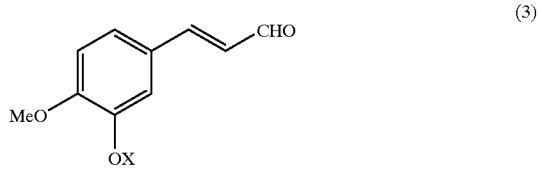

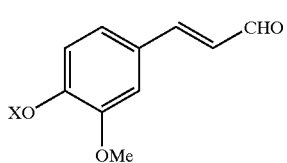

wherein in formulae (3'), (4'), (3) and (4), Me denotes a methyl group, and in the above formulae (3) and (4), X denotes any one of lithium atom, sodium atom, and potassium atom.

10. The process of claim 1, which further comprises a process for converting said compound of formula (1) from a salt form obtained in said reductive alkylation reaction, into the free form through neutralization with an acid.

11. The process of claim 10, wherein said acid is at least one selected from the group consisting of hydrochloric acid, sulfuric acid, acetic acid, and mixtures thereof.

12. The process of claim 10, wherein in said reductive alkylation reaction, said neutralization with an acid is conducted during said hydrogenation reaction.

13. The process of claim 1, wherein said reductive alkylation reaction is conducted at a temperature in a range of 0 to 60° C.

14. The process of claim 1, which further comprises forming a reaction mixture comprising said aspartame, said aldehyde, and said base, and holding said reaction mixture while stirring for at least 10 minutes at a temperature of 40° C. or lower before hydrogenation.

15. The process of claim 1, wherein said catalyst is at least one selected from the group consisting of palladium on carbon, palladium black, Raney Nickel, platinum on carbon, and mixtures thereof.

16. The process of claim 1, wherein said reductive alkylation reaction is conducted in a solvent, and said solvent is methanol.

17. The process of claim 1, wherein said reductively alkylating comprises a hydrogenation reaction with a hydrogen pressure of 0.1 to 10 MPa.

18. The process of claim 1, wherein said compound of formula (2) is in the free form, and which further comprises a process for crystallization of said free form with a mixed solvent of water-alcohol.

19. The process of claim 18, wherein said alcohol is methanol.

20. The process of claim 1, wherein in said formula (2), $R_1$ is a hydrogen atom, a methyl group or a methoxy group, $R_2$ is a hydrogen atom, a methyl group or a methoxy group, $R_3$ is a hydroxyl group, and $R_4$ and $R_5$ are a hydrogen atom, and in formula (1), $R_1$ is a hydrogen atom, a methyl group or a methoxy group, $R_2$ is a hydrogen atom, a methyl group or a methoxy group, $R_3$ is a benzyloxy group, and $R_4$ and $R_5$ are a hydrogen atom.

21. The process of claim 1, wherein in said formula (2), $R_1$, $R_4$ and $R_5$ are a hydrogen atom, $R_2$ is a hydroxyl group, and $R_3$ is a methoxy group, and in formula (1), $R_1$, $R_4$ and $R_5$ are a hydrogen atom, $R_2$ is a benzyloxy group, and $R_3$ is a methoxy group.

22. The process of claim 1, wherein said base is selected from the group consisting of LiH, NaH, KH, LiOMe, NaOMe, KOMe, LiOH, NaOH, KOH, Mg(OH)$_2$, sodium carbonate, sodium hydrogen carbonate, triethyl amine, diethyl amine, and mixtures thereof.

23. The process of claim 2, wherein said base is at least one member selected from the group consisting of LiH, NaH, KH, LiOMe, NaOMe, KOMe, LiOH, NaOH, KOH, Mg(OH)$_2$, sodium carbonate, sodium hydrogen carbonate, triethyl amine, diethyl amine, and mixtures thereof.

24. The process of claim 3, wherein said base is at least one member selected from the group consisting of LiH, NaH, KH, LiOMe, NaOMe, KOMe, LiOH, NaOH, KOH, Mg(OH)$_2$, sodium carbonate, sodium hydrogen carbonate, triethyl amine, diethyl amine, and mixtures thereof.

25. The process of claim 20, wherein said base is at least one member selected from the group consisting of LiH, NaH, KH, LiOMe, NaOMe, KOMe, LiOH, NaOH, KOH, Mg(OH)$_2$, sodium carbonate, sodium hydrogen carbonate, triethyl amine, diethyl amine, and mixtures thereof.

26. The process of claim 21, wherein said base is at least one member selected from the group consisting of LiH, NaH, KH, LiOMe, NaOMe, KOMe, LiOH, NaOH, KOH, Mg(OH)$_2$, sodium carbonate, sodium hydrogen carbonate, triethyl amine, diethyl amine, and mixtures thereof.

* * * * *

UNITED STATES PATENT AND TRADEMARK OFFICE
CERTIFICATE OF CORRECTION

PATENT NO. : 6,822,111 B2
DATED : November 23, 2004
INVENTOR(S) : Shigeru Kawahara, Kazutaka Nagashima and Tadashi Takemoto It is certified that error appears in the above-identified patent and that said Letters Patent is hereby corrected as shown below:

Column 12,
Line 67, "derivative" should read -- compound --.

Column 13,
Line 67, "which comprises" should read -- which further comprises --.

Signed and Sealed this

Tenth Day of May, 2005

JON W. DUDAS
*Director of the United States Patent and Trademark Office*